United States Patent [19]
Hutchinson

[11] Patent Number: 5,965,571
[45] Date of Patent: Oct. 12, 1999

[54] CHOLINESTERASE INHIBITORS FOR TREATMENT OF PARKINSON'S DISEASE

[75] Inventor: Michael Hutchinson, New York, N.Y.

[73] Assignee: New York University, New York, N.Y.

[21] Appl. No.: 08/915,736

[22] Filed: Aug. 21, 1997

Related U.S. Application Data

[60] Provisional application No. 60/022,746, Aug. 22, 1996.
[51] Int. Cl.$^6$ ...................................................... A01N 43/44
[52] U.S. Cl. ............................ 514/297; 514/32; 514/278; 514/411; 424/489
[58] Field of Search ............................. 514/32, 278, 411, 514/297; 424/489

[56] References Cited

U.S. PATENT DOCUMENTS

| | | | |
|---|---|---|---|
| 4,948,807 | 8/1990 | Rosin et al. | 514/484 |
| 5,585,378 | 12/1996 | Boar et al. | 514/253 |
| 5,668,117 | 9/1997 | Shapiro | 514/55 |

*Primary Examiner*—Thurman K. Page
*Assistant Examiner*—Lakshmi Channavajjala
*Attorney, Agent, or Firm*—Browdy and Neimark

[57] ABSTRACT

Parkinson's disease can be treated with an at least one cholinesterase inhibitor. The cholinesterase inhibitor has been found to alleviate both any symptoms of dementia as well as to reduce rigidity and improve motor function.

16 Claims, No Drawings

CHOLINESTERASE INHIBITORS FOR TREATMENT OF PARKINSON'S DISEASE

CROSS REFERENCE TO RELATED APPLICATION

The present application claims priority from U.S. provisional application Ser. No. 60/022,746, filed Aug. 22, 1996, the entire contents of which are hereby incorporated herein by reference.

FIELD OF THE INVENTION

The present invention is directed to the use of cholinesterase inhibitors in treating rigidity and dementia associated with Parkinson's disease.

BACKGROUND OF THE INVENTION

Parkinson's disease is a chronic nervous disease characterized by fine, slowly spreading tremors, rigidity, and a characteristic gait. Although the onset of Parkinson's disease may be abrupt, it generally occurs gradually. The initial symptom is often a fine tremor beginning in either a hand or a foot which may spread until it involves all of the members. The duration of Parkinson's disease is indefinite, and recovery rarely if ever occurs. A psychotic confusional state may be seen in the later stages of Parkinson's disease, which is a common and significant source of morbidity.

Levodopa has historically been the medication of choice in treating Parkinson's disease, and there are rarely any failures with levodopa therapy in the early years of treatment. Unfortunately, this response is not sustainable. Most patients develop adverse effects after long-term usage of levodopa; in fact, in some the benefits of treatment wane as the disease progresses.

Several common types of central nervous system dysfunction and peripheral side effects are associated with administration of levodopa. Toxic side effects to the central nervous system include mental changes, such as confusion, agitation, hallucinosis, hallucinations, delusions, depression, mania and excessive sleeping. The symptoms may be related to activation of dopamine receptors in non-striatal regions, particularly the cortical and limbic structures. Elderly patients and patients with cortical Lewy body disease or concomitant Alzheimer's disease are extremely sensitive to small doses of levodopa. However, all patients with Parkinson's disease, regardless of age, can develop psychosis if they take excess amounts of levodopa as a means to overcome "off" periods. This is difficult to remedy, as reducing the dosage of levodopa may lessen its beneficial influence on motor function.

Although dementia may be associated with Parkinson's disease, Alzheimer's disease and Parkinson's disease are pathologically very distinct. Senile dementia of the Alzheimer type (SDAT) is associated with degeneration of the nucleus basalis, and consequently with a cholinergic deficit. Alzheimer's disease is characterized by plaques and neurofibrillary tangles, mainly in the cerebral cortex. Parkinson's disease, on the other hand, is characterized by distinctive Lewy bodies, which are eosinophilic, cytoplasmic structures found mainly in small nuclei at the base of the brain, especially the substantia nigra (dopaminergic cells) and nucleus basalis (cholinergic cells). These two diseases are clinically distinguishable to a competent practitioner.

Clinically, Alzheimer's disease presents with personality change, language errors (difficulties with categorical speed and word generation) and loss of short term memory. The patient is usually alert and attentive. The condition may or may not progress to include mild rigidity of the muscles, although rigidity is never the presenting complaint.

Parkinson's disease, in contrast, presents with muscular rigidity, tremor and imbalance. It may or may not progress to include dementia, although dementia is never the presenting complaint. When dementia is present in Parkinson's patients, it is clinically distinguishable from Alzheimer's disease, and is characterized by inattention, visual hallucinations, and a worsening of the confusion produced by administration of levodopa.

Prior to the introduction of levodopa, anticholinergic drugs had been the conventional treatment of mild parkinsonism since the discovery of belladonna alkaloids in the mid-nineteenth century. However, these drugs have a propensity for exacerbating dementia. Nevertheless, since anticholinergic drugs are known to ameliorate rigidity in the early stages of the disease, the conventionally skilled neurologist would instinctively believe that a procholineric drug might worsen rigidity, as central cholinergic activity appears to be important for memory function in Parkinson's disease. Unfortunately, patients receiving anticholinergic drugs for parkinsonism may experience reversible cognitive deficits so severe as to mimic Alzheimer's disease. Identical memory disturbances have been produced by administration of atropine to patients with either Alzheimer's disease or Parkinson's disease with dementia.

Recent trials using cholinesterase inhibitors, such as tacrine, have shown promise for partial reversal of senile dementia of the Alzheimer type in a few patients. Ott et al., in *Clinical Neuropharmacology* 15(4):322–325, 1992, treated a patient with Alzheimer's disease with tacrine, which has traditionally been used to treat Alzheimer's dementia. The individual originally presented as Alzheimer's disease developed other symptoms, including extrapyramidal features. This patient, along with three other patients with a typical presentation of Alzheimer's disease responded with improvement or stabilization in cognitive ability and activities of daily living score. Another case, again clinically and neuropathologically diagnosed as Alzheimer's disease, responded initially, but this response was not sustained. This paper clearly implies, then, that increasing rigidity would be expected in a Parkinson patient to whom tacrine is administered, since the tacrine caused rigidity in an Alzheimer's patient. This would certainly deter a practicing neurologist from prescribing this type of drug for a patient suffering from Parkinson's disease, as any medication that increases rigidity would be contraindicated for parkinsonian patients.

Treatment of dementia in parkinsonian patients with cholinomimetic drugs presents a dilemma, since the movement disorder would be expected to worsen with treatment with tacrine or similar anticholinesterase medications. It should be noted that Ott et al., ibid., treated an Alzheimer's patient with mild parkinsonism, rather than a patient whose primary presentation was Parkinson's disease, with a combination of levodopa and tacrine. The dramatic increase in tremor, as well as induction of gait dysfunction and subjective feelings of rigidity, were attributed to the cholinergic effects of acetylcholinesterase inhibitors on the striatum. The increased tremor responded to addition of levodopa as well as to decrease in tacrine dosage with restoration of baseline function after either maneuver. After two months of treatment with levodopa, the gait function and bradykinesia appeared to improve, suggesting that the patient had developed some tolerance to the extra-pyramidal effects of tacrine. It had not been determined whether such tolerance actually occurs and whether it would be sustained, or whether levodopa actually improved it.

Perry et al., in *Annals New York Academy of Sciences* pp. 197–202, report examining cholinergic and monoaminergic (dopaminergic and serotonergic) activities in postmortem brain tissue in senile dementia of Lewy body type, Parkinson's disease, and Alzheimer's disease. The quantitative data they obtained suggested that although extra-pyramidal symptoms relate to striatal levels of dopamine, cognitive impairment was most closely associated with cholinergic but not monoaminergic deficits in temporal and archicortical areas. For example, hallucinations, frequently manifested in Lewy body dementia, appear to be related to an extensive cholinergic deficit in temporal neocortex and the resulting imbalance between decreased cholinergic and relatively preserved serotonergic activities.

As with Lewy body dementia, Parkinson's disease is associated with a cholinergic deficit, which may be more profound than that seen in senile dementia of the Alzheimer type (SDAT). Later stages of Parkinson's disease are characterized by a debilitating confusional state with psychotic features. Although this may, to some extent, overlap symptoms of SDAT, there is presumably a high incidence of pure Lewy body dementia in parkinsonian patients with dementia. As anticholinergic drugs have mild antiparkinsonian effects, however, it has been assumed that a procholinergic drug will worsen the characteristic rigidity of Parkinson's disease.

SUMMARY OF THE INVENTION

It is an object of the present invention to overcome all of the aforementioned defects of the prior art.

It is another object of the present invention to treat the rigidity associated with Parkinson's disease.

It is another object of the present invention to treat the dementia associated with Parkinson's disease.

According to the present invention, Parkinson's disease is treated by administering a cholinesterase inhibitor to patients suffering from Parkinson's disease. It was found that the cholinesterase inhibitor not only improved the dementia associated with Parkinson's disease, contrary to prior expectations, but it also decreased rigidity and improved motor function in patients undergoing treatment.

At least one cholinesterase inhibitor is administered to Parkinsons' patients in amounts effective to improve motor function and decrease the dementia associated with the disease. The cholinesterase inhibitor may be administered in combination with levodopa or other medications conventionally administered to patients with Parkinson's disease.

DETAILED DESCRIPTION OF THE INVENTION

According to the present invention, patients with Parkinson's disease are treated with at least one cholinesterase inhibitor to effect the following physiological improvements: restored motor function; improved orientation, attention and awareness; and elimination of hallucinations (where present).

Acetylcholinesterase inhibitors impede acetylcholine metabolism by inhibiting the enzyme acetylcholinesterase. Since the action of acetylcholine is terminated by its rapid hydrolysis into choline and acetic acid, acetylcholinesterase inhibitors prolong or mimic the action of the neurotransmitter acetylcholine.

Acetylcholine is released into synapses where it behaves as a neurotransmitter that associates with macromolecular receptors. The association of acetylcholine with its receptors initiates a physiological response, probably by opening membrane ion channels.

The acetylcholine receptors appear to consist of two general subtypes. One subtype relies upon nicotine as an agonist (that is, the nicotine molecule appears to fit into the one subtype of acetylcholine receptor). For example, the nicotinic effect of acetylcholine becomes apparent when its degradation by acetylcholinesterase is inhibited as discussed by Vidal et al., *Neuroscience* 29 (2), pp. 261–270 (1989).

The other general subtype of acetylcholine receptors is muscarine. Muscarine is an alkaloid that mimics the action of acetylcholine or muscarinic receptors.

Activation of cholinergic receptors results in bradycardia, increased secretion (e.g., salivary and sweat), and gastrointestinal contractions, among other symptoms. Hypotensive, cardiac inhibitory effects caused by low doses of acetylcholine are similar to those produced by muscarine and appear to be mediated via muscarinic acetylcholinergic receptors at post-ganglionic parasympathetic terminals. In contrast, effects at autonomic ganglia and neuromuscular junctions result from nicotinic acetylcholine receptors.

Many cell membranes can be excited by specific chemical or physiological stimuli. The common features of these processes and other carried out by excitable assemblies are:

(1) The stimulus is detected by a highly specific protein receptor, which is an integral component of the excitable membrane.

(2) The specific stimulus elicits a conformational change in the receptor. Consequently, the permeability of the membrane or the activity of a membrane-bound enzyme changes. Many of the responses are highly amplified.

(3) The conformational changes exhibited by the protein receptor molecule and the resulting alterations in function are reversible. In other words, there exist mechanisms that return the receptor to its resting state and restore its excitability.

Nerve cells interact with other nerve cells at junctions called synapses. Chemical transmitters, small diffusable molecules such as acetylcholine and norepinephrine, permit nerve impulses to communicate across synapses. Acetylcholine also serves as the transmitter at motor end plates (neuromuscular junctions), the junctions between nerve and striated muscle.

The presynaptic membrane of a cholinergic synapse, i.e., one that utilizes acetylcholine as its neurotransmitter, is separated from the postsynaptic membrane by a gap of about 500 Å called the synaptic cleft. The end of the presynaptic axon is filled with synaptic vesicles containing acetylcholine. The arrival of a nerve impulse triggers the release of acetylcholine into the cleft. The acetylcholine molecules then diffuse to the postsynaptic membrane, where they combine with specific receptor molecules. This produces a depolarization of the postsynaptic membrane, which is propagated along the electrically excitable membrane of the second nerve cell. Acetylcholine is hydrolyzed by acetylcholinesterase and the polarization of the postsynaptic membrane is restored.

Acetylcholine is synthesized near the presynaptic end of axons by the transfer of an acetyl group from acetyl CoA (Co-enzyme A) to choline. Some of the acetylcholine is taken up by synaptic vesicles and the remainder stays in the cytosol. A cholinergic synaptic vesicle, typically measuring 400 Å in diameter, contains about 104 acetylcholine molecules.

Acetylcholine is released from the presynaptic membrane in the form of "packets" containing approximately 104 molecules. The quantity of packets released depends upon the potential of the individual presynaptic membrane. In other words, the release of acetylcholine is an electrically controlled form of secretion.

This release of acetylcholine depends on the concentration of $Ca^{2+}$ in the extracellular fluid. The depolarization of the presynaptic membrane permits the entry of calcium ions into the cell. Entering $Ca^{2+}$, in turn, promotes a transient fusion of the synaptic vesicle membrane and the presynaptic membrane.

The amount of acetylcholine released from the presynaptic membrane varies according to the ambient $Ca^{2+}$ concentration. It is important to note that all acetylcholine is released in the aforementioned "packets" of approximately 104 acetylcholine molecules. However, the number of "packets" released, and therefore the total amount of acetylcholine released, is governed by the presynaptic action potential established by the conentration of calcium ions surrounding the presynaptic membrane.

The depolarizing signal may be switched off to restore the excitability of the postsynaptic membrane. For example, acetylcholine is hydrolyzed to acetate and choline by acetylcholinesterase. Acetylcholinesterase, located in the synaptic cleft, is bound to a network of collagen and glycosaminoglycans derived from the post-synaptic cell. The 260-kDa enzyme, which has an $\alpha 2\beta 2$ structure, can be readily separated form the acetylcholine receptor.

Acetylcholinesterase has a very high turnover number of $25,000s^{-1}$, which means that it cleaves an acetylcholine molecule in 40 microseconds. The high turnover number of the enzyme is essential for the rapid restoration of the polarized state of the post synaptic membrane. Synapses can transmit 1000 impulses per second only if the postsynaptic membrane recovers its polarization within a fraction of a millisecond.

Acetylcholine reacts with a specific serine residue at the active side of acetylcholinesterase to form a covalent acetyl-enzyme intermediate, and choline is released. The acetyl-enzyme intermediate then reacts with water to form acetate and regenerate the free enzyme.

Postsynaptic acylcholine receptors may be assigned to two pharmacologically distinguishable classes. Nicotinic type receptors, found in the ganglia, can be stimulated by nicotine and may be blocked by curare. The distinctly different muscarinic type receptors, located in the effector organs, are stimulated by muscarine and, unlike the nicotinic receptors, are insensitive to curare.

As mentioned, acetylcholinesterase is found at post synaptic membranes; it is also present in the erythrocytes and in the plasma Erythrocytic and plasmic acetylcholinesterase are referred to as un-specific acetylcholinesterases or pseudocholinesterases or butyrylcholinesterases.

Acetylcholinesterase inhibitors enhance the effect of acetylcholine by either inhibiting its hydrolyzation or by prolonging the actual time that each acetylcholine molecule is present in the synapse. Cholinesterase inhibitors, considered equivalent to anticholinesterase, may also be known as a cholinesterase agonist.

Cholinergic synapses are found in the motor and plates (neuromuscular junctions), in the sympathetic part of the autonomic nervous system in all ganglionic synapses, at the synapses in the adrenal medulla, and at postsynaptic synapses in the sweat glands. In the ganglia and post ganglionic effector synapses of the parasympathetic autonomic nervous system, acetylcholine serves as a transmitter. Furthermore, acetylcholine is believed to function as a neurotransmitter in the central nervous system.

Currently, the known acetylcholinesterase inhibitors available include galanthamine, physostigmine, tetrahydroaminoacridine (tacrine), citicoline, velnacrine maleate, metrifonate, and heptastigmine. For purposes of the present invention, "cholinesterase inhibitors" includes acyl cholinesterase inhibitors, including acetylcholinesterase inhibitors and butyryl cholinesterase inhibitors.

Tacrine, a reversible cholinesterase inhibitor, is known chemically as 1,2,3,4-tetrahydro-9-acridinamine (commonly referred to in clinical and pharmacological literature as THA). Tacrine is an orally bioavailable, centrally active, reversible cholinesterase inhibitor. Presumably, its efficacy lies in its ability to elevate acetylcholine concentrations in the cerebral cortex by allowing the degradation of acetylcholine released by those cholinergic nerurons that remain intact.

Consequently, tacrine and other cholinesterase inhibitors have been used to treat dementia associated with Alzheimer's disease. Tacrine is rapidly absorbed after oral administration, with maximum plasma concentrations occurring within one to two hours. The drug is extensively metabolized by the cytochrome P450 system into multiple metabolites.

A study conducted on the use of cholinesterase inhibitors in patients suffering from Parkinson's disease demonstrated the effects of tacrine on rigidity and dementia. Seven patients were selected for the study, five men and two women, ranging in age from 66 to 82, with a mean age of 73.9 years. The patients were selected according to the following criteria: (a) diagnosis of Parkinson's disease prior to the onset of dementia; (b) rigidity that had initially responded to levodopa; (c) a confusional state incorporating visual hallucinations and exacerbated by dopaminergic drugs; (d) a normal brain MRI or CT within two months of the study, to exclude multi-infarct dementia and reduce the possibility of concurrent senile dementia of the Alzheimer's type.

All of the patients studied had carried the diagnosis of Parkinson's disease for several (three to 18) years prior to the onset of dementia. The diagnosis was made in each case on the basis of a syndrome of progressive rigidity and bradykinesia. Four patents also had a mild resting tremor at the time of diagnosis. In each case these presenting symptoms had initially responded well to levodopa, and all patients were taking levodopa at the time of entry into the study. No patient had exhibited dyskinesia as a result of treatment with levodopa. None of the patients was currently using dopamine agonists, although four of the patients had previously used these drugs but had discontinued them because of worsening confusion. Selegiline had also been used in all of the patients before this study, and in all patients selegiline had been discontinued for the same reason. None of the patients had used selegiline within four months of the start of the study.

Four subjects had severe motor disability (Hoehn and Yahr stage 5) and were confined to a wheelchair or were bedridden. Two patients were stage 4, and could walk with assistance. One patient was stage 3, but had had a recent series of falls. The patients were tested for baseline serum glutamic oxaloacetic transaminase and glutamic pyruvic transaminase levels and were started on 10 mg of tacrine four times daily. Liver function tests were obtained on a weekly basis. After two weeks, if the transaminase concentrations remained stable, the dose was increased to 20 mg tacrine three times daily and maintained at that level for at least two months. All patients underwent Folstein (mini mental) testing immediately before treatment, and again after two months of treatment. Unified Parkinson's disability rating scale (UPDRS) scores were also obtained before and after treatment, the motor categories by direct examination, and the daily activity scores by interview of the spouse or caregiver. All patients were maintained on levodopa without change during the trial.

In all cases the frequency of hallucinations was greatly reduced after treatment, and in five cases hallucinations were essentially eliminated. All seven patients showed much improvement in both Folstein scores (mean improvement 7.1, range 3–13, P<0.0001) and UPDRS scores (items 1–31: mean score before treatment 79.3, mean score after treatment 29.6, P<0.0001). These results are shown in the Table.

TABLE

Dementia and motor disability scores in Parkinson's disease before, and two months after, treatment with tacrine

| PATIENT | AGE (yrs) | PD (yrs) | DEMENTIA (yrs) | MMS pre-Rx | MMS post-Rx | UPDRS pre-Rx | UPDRS post-Rx |
|---|---|---|---|---|---|---|---|
| 1 | 82 | 4 | 1 | 21 | 24 | 34 | 17 |
| 2 | 72 | 2 | .5 | 15 | 24 (28*) | 89 | 25 (8*) |
| 3 | 77 | 6 | 1 | 15 | 23 | 91 | 31 |
| 4 | 69 | 15 | 2 | 15 | 21 | 86 | 28 |
| 5 | 78 | 4 | 1 | 15 | 26 | 87 | 44 |
| 6 | 66 | 5 | .5 | 16# | 24# | 65 | 21 |
| 7 | 74 | 4 | .25 | 19 | 24 | 103 | 41 |

PD = Parkinson's disease duration
MMS = Mini Mental Score (Folstein) out of 30
UPDRS = Unified Parkinson Disability Rating Scale (items 1–31)
pre/post Rx = before/after treatment
*at 7 months after initiation of treatment
scored out of 29

There was no characteristic pattern of mental change. However, marked improvements were seen in the categories of orientation, attention (serial 7's), and visuospatial awareness (copying a geometric figure). Additionally, patients were able to walk independently, with the improvements in gait corresponding roughly to improvements in mentation. There was no characteristic patten of motor improvement, and in most patients improvements were seen in most categories of the UPDRS. The specifics are described below.

Patient #1, an 82 year old man with a four year history of Parkinson's disease, had a two year history of progressive imbalance with frequent falls. He had a one year history of progressive memory loss, particularly in remembering names and faces, with rare visual hallucinations.

After treatment with tacrine, Patient #1 reported a subjective improvement in his sense of balance in the first week of treatment, and stopped falling thereafter. In addition, he no longer experienced hallucinations. Cognitive improvements at two months were modest compared to the remaining patients treated, although he had the highest level of pre-treatment function. Improvements have been maintained for nine months.

Patient #2, a 72 year old woman with a two year history of Parkinson's disease, had a six month history of rapid physical decline resulting in her dependence upon the use of a wheelchair. During the same six month period she developed a progressive dementia with frequent formed visual hallucinations. As her confusional state deepened, she became progressively more withdrawn from her family. She also exhibited urinary incontinence and frequent benign visual hallucinations.

Within two days after tacrine treatment began, Patient #2 was walking without assistance. At the same time her hallucinations were essentially eliminated, and she showed marked improvements in mentation and sociability. In addition, she became continent. Not only were her improvements maintained, but she appeared to improve further.

Patient #3 was a 77 year old man with a six year history of Parkinson's disease and a one year history of progressive dementia with hallucinations. He had been hospitalized in a rehabilitation facility in fruitless attempts to improve his gait. Concurrently, he demonstrated consistent confusion and a tendency to wander, with disruptive nocturnal agitation. Within two days of initiation of tacrine, however, the agitation had disappeared and he showed progressive mental and physical improvements. Indeed, he was able to walk out of the hospital five days later, in the words of his family, "back to his old self."

These improvements were maintained on a dose of 60 mg. tacrine daily. Two months later, after his post-treatment evaluation, his serum SGOT and SGPT levels and risen above 300 and the tacrine was abruptly discontinued. At that time his Folstein score had been 23. Within 24 hours of discontinuing tacrine he had progressive worsening of gait and balance, as well as increased confusion. Within three days his dementia was so profound that he was essentially untestable, requiring further hospitalization for observation. He was administered tacrine and re-challenged four days later, exhibiting rapid progressive improvements in cognition which have been maintained over the subsequent ten months. About five months after this re-challenge his rigidity began to progress slightly, but improved again on bromocriptene, a drug previously intolerable due to his worsening confusional state. Hallucinations, too, were eliminated.

Patient #4, age 69, had a two year history of dementia with hallucinations, and rigidity that responded only minimally to levodopa. Indeed, increases in levodopa often exacerbated confusion and agitation. Within a week of initiating tacrine therapy, she proved increasingly sociable and began walking unassisted. Her mental and physical improvements persisted for six months. However, she later showed a progressive decline despite increased tacrine dosages of 160 mg. daily. Her new b aseline is, however, somewhat higher than her p re-treatment level of functioning.

Patient #5 showed little improvement on the lowest dose of tacrine administered, 40 mg daily. However, on the higher dose of 60 mg daily he showed rapid progressive advancements in mentation, gait and balance. These improvements have been sustained for six months.

Patient #6 responded markedly to tacrine. Hallucinations disappeared and, after the first week of medication therapy (at the lowest dose of 40 mg. daily), improvements in mentation, gait, and balance proved sufficient to cancel a planned hospitalization at a rehabilitation facility. Additionally, this patient's severe constipation was ameliorated upon regular administration of tacrine. These improvements have been maintained for seven months.

Patient #7, age 74, had been bedridden for one month and wheelchair-bound for three months previously. However, following the initial week of treatment, he was able to walk with assistance. On higher doses of tacrine (60 mg. daily), he began walking unassisted. Improvements in both mentation and gait have been maintained for ten months, while hallucinations have markedly declined.

In a separate trial, a 78 year old patient with Parkinson's disease was assessed as having a Mini Mental Score (MMS) of 11/30 (i.e., 11 points out of a maximum of 30). A score of 26/30 represents the lower limit of normal; 11/30, then, is suggestive of a profoundly demented state.

The same patient scored 109/124 on the Unified Parkinson's Disease Rating Scale (UPDRS), indicating a degree of rigidity so advanced as to immobilize the patient, even in bed. Moreover, the patient tended to fall backwards spontaneously, rendering him unable to walk even with extensive assistance.

Upon administration of 40 mg. tacrine (10 mg. four times) daily, building up to 60 mg. daily after seven weeks, the patient exhibited remarkable improvements in dementia and rigidity. His Mini Mental Score increased to 20/30, denoting only mild to moderate dementia. His score on the Unified Parkinson's Disease Rating Scale dropped to 51/124, representing a significant reduction in rigidity. Indeed, he can now get out of a chair and walk without assistance.

The successes recorded in the above studies clearly indicate improved mental and physical states in patients receiving tacrine therapy. Improvements in motor disability scores were an unexpected, but welcome, result of the medication. Before starting this study it was thought that, even if the dementia ameliorated, patients might exhibit increased rigidity, since anticholinergic drugs have slight antiparkinson motor effects. However, contrary to expectations, the patients treated with the cholinesterase inhibitor became less rigid.

Cholinesterase inhibiting agents can be administered alone to patients with Parkinson's disease, or, preferably, are administered in combination with levodopa or other medications used to treat the symptoms of Parkinson's disease. Medicaments are considered to be provided "in combination" with one another if they are provided to the patient concurrently or if the time between the administration of each medicament is such as to permit an overlap of biological activity.

Pharmaceutical compositions for administration according to the present invention can comprise at least one cholinesterase inhibitor in a pharmaceutically acceptable form optionally combined with a pharmaceutically acceptable carrier. These compositions can be administered by any means that achieve their intended purposes. Amounts and regimens for the administration of a composition according to the present invention can be determined readily by those with ordinary skill in the art of treating Parkinson's disease.

For example, one may administer the treatment orally, or, alternatively or concurrently, by parenteral administration, such as subcutaneous, intravenous, intramuscular, intraperitoneal, transdermal, or buccal routes. The dosage administered depends upon the age, health and weight of the patient, type of previous or concurrent treatment, if any, frequency of treatment, and the nature of the effect desired.

Compositions within the scope of this invention for treating Parkinson's disease include all compositions comprising at least one cholinesterase inhibitor in an amount effective to achieve its intended purposes. While individual needs vary, determination of optimal ranges of effective amounts of each component is within the skill of the art. Typical dosages of cholinesterase inhibitor for treating Parkinson's disease comprise about 5 mg to 200 mg per day, administered in doses of from one to four times daily. Of course, the dosage will vary with the degree of rigidity and dementia experienced by the patient, the patient's response the the cholinesterase inhibitor, and the administration of other drugs for treating Parkinson's disease, e.g., levodopa.

In addition to pharmaceutically active compounds, compositions for treating Parkinson's disease according to the present invention can also contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, troches and capsules, and also preparations which can be administered rectally, such as suppositories, as well as suitable solutions for administration by injection or orally, contain from about 0.1 to 99 percent, preferably from about 20 to 75 percent of active compound(s), together with the excipient.

Pharmaceutical preparations for treating Parkinson's disease according to the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture, and processing the mixture of granules, after adding suitable auxiliaries, if desired or necessary, to obtain tablets or dragee cores.

Suitable excipients are, e.g., fillers such as saccharides, for example, lactose or sucrose, mannitol or sorbitol; cellulose derivatives; zinc compounds; calcium phosphates such as tricalcium phosphate or calcium hydrogen phosphate; as well as binder such as starch paste, using, for example, maize starch, wheat starch, rice starch, potato starch; gelatin; tragacanth; and/or polyvinylpyrrolidone.

Auxiliaries include flow-regulating agents and lubricants, such as silica, talc, stearic acid or salts thereof, and/or polyethylene glycol. Dragee cores are provided with suitable coatings which, if desired, are resistant to gastric juices. For this purpose, concentrated saccharide solutions can be used, which can optionally contain gum arabic, talc, polyvinyl pyrrolidione, polyethylene glycol and/or titanium dioxide, lacquer solutions and suitable organic solvents or solvent mixtures. In order to produce coatings resistant to gastric juices, i.e., enteric coatings, solutions of suitable cellulose preparations such as acetylcellulose phthalate or hydroxypropylmethyl cellulose phthalate are used. Dyestuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which can be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers may be added.

The cholinesterase inhibitors of the present invention can also be administered in the form of an implant when compounded with a biodegradable slow-release carrier. Alternatively, the active ingredients can be formulated as a transdermal path for continuous release of the active ingredient.

In light of studies of tacrine in Alzheimer's disease[1,2], the speed of response in Parkinson's dementia according to the present invention proved surprising, particularly since tacrine was administered in such low doses. Most patients showed motor improvements within two or three days of initiation of treatment, and all patients showed further rapid improvements at the higher dose (60 mg and above). This type of response is seen with initiation of levodopa or selegiline treatment of Parkinson's disease, and it is not surprising in that context, i.e., when the concentration of a given neurotransmitter is low, any increase will lead to rapid improvements in the functions served by that neurotransmitter.

The psychotic confusional state seen in the later stages of Parkinson's disease is a prevalent and significant source of morbidity. The results of treating Parkinson's disease patients with low doses of a cholinesterase inhibitor has been demonstrated to be highly effective in treatment of this confusional state. Treatment with a cholinesterase inhibitor obviated the need to treat patients with conventionally used anti-psychotic medications. Moreover, the cholinesterase inhibitors also improved motor function in patients afflicted with Parkinson's disease.

The foregoing description of the specific embodiments will so fully reveal the general nature of the invention that others can, by applying current knowledge, readily modify and/or adapt for various application such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

All references cited in this specification are hereby incorporated by reference.

REFERENCES

1. Knapp, M J, Knopman D S, Solomon P R, Pendlebury W W, Davis C S, Gracon S I. A 30-wek randomized controlled trial of high-dose tacrine in patients with Alzheimer's disease. The Tacrine Study Group [see comments]. *JAMA* 1994; 271:985–991.

2. Davis K L, Thal L J, Gamzu E R, et al. A double-blind, placebo-controlled multicenter study of tacrine for Alzheimer's disease. The Tacrine Collaborative Study Group [see comments]. *N. Engl. J. Med.* 1992;327:1253–1259.

3. Lahiri D K, Lewis S, Farlow M R. Tacrine alters the secretion of the beta-amyloid precursor protein in cell lines. *J. Neurosci. Res.* 1994;37:777–787.

4. Nordberg A. Effect of long-term treatment with tacrine (THA) in Alzheimer's disease as visualized by PET. *Acta Neurologi ca Scandinavica* 1993;149:62–65.

5. McKeith I G, Petry R H, Fairbairn A F, Jabeen S, Perry E K. Operational criteria for senile dementia of Lewy body type (SDLT). *Psychological Medicine* 1992;22:911–922.

6. Wilcock G K, Scott M I. Tacrine for senile dementia of Alzheimer's or Lewy body type [letter; comment]. *Lanc* 1994;344:544.

7. Perry E K, Haroutunian V, Davis K L, et al. Neocortical cholinergic activities differentiate Lewy body dementia from classical Alzheimer's disease. *Neuroreport* 1994;5:747–749.

8. Levy R, Eagger S, Griffiths M. et al. Lewy bodies and response to tacrine in Alzheimer's disease [letter] [see comments]. *Lanc* 1994;343:176.

9. Nakano L, Hirano A. Parkinson's disease: neuron loss in the nucleus basalis without concomitant Alzheimer's disease. *Annals of Neurology* 1984;15:415–418.

10. De Leon M J, Golomb J, George A E, et al. The radiologic prediction of Alzheimer disease: the atrophic hippocampal formation. *Ajnr: American Journal of Neuroradiology* 1993;14:897–906.

11. Folstein M, Folstein S, McHugh P R. "Mini-Mental Status". A practical method for grading the cognitive state of patients for the clinician. *J. Psychiatr. Res.* 1975;12:189.

12. Fahn S, Elton E R. Unified Parkinson Disease Rating Scale, in:Fahn S, Marsden C D, Calne D, Goldstein M, eds. *Recent Developments in Parkinson's Disease* Floral Park, N.J.: Macmillan 1987;2:293–304.

13. Ott B R, Lannon M C. Exacerbation of parkinsonism by tacrine. *Clin Neuropharmacol* 1992;15:322–325.

What is claimed is:

1. A method for treating a patient suffering from Parkinson's Disease consisting of administering to said patient an effective amount of at least one cholinesterase inhibitor to treat symptoms of Parkinson's Disease.

2. The method according to claim 1, wherein the patient is treated for rigidity associated with Parkinson's Disease.

3. The method according to claim 1, wherein the patient is treated for dementia associated with Parkinson's Disease.

4. The method according to claim 1, wherein the cholinesterase inhibitor is an acetylcholinesterase inhibitor.

5. The method according to claim 4, wherein the acetylcholinesterase inhibitor is selected from the group consisting of galanthamine, physostigmine, tetrahydroamino-acridine (tacrine), citicoline, velnacrine maleate, metrifonate, and heptastigmine.

6. The method according to claim 4, wherein the cholinesterase inhibitor is a butyrylcholinesterase inhibitor.

7. The method according to claim 4, wherein the at least one cholinesterase inhibitor is administered in an amount of from about 20 mg to about 200 my per day.

8. A method for treating a patient suffering from Parkinson's Disease consisting of administering to said patient an effective amount of at least one cholinesterase inhibitor in combination with at least one medication conventionally administered to treat Parkinson's Disease.

9. The method according to claim 8, wherein said at least one medication is levodopa.

10. The method according to claim 8, wherein said at least one medication is selegilene.

11. The method according to claim 8, wherein the patient is treated for rigidity associated with Parkinson's Disease.

12. The method according to claim 8, wherein the patient is treated for dementia associated with Parkinson's Disease.

13. The method according to claim 8, wherein the cholinesterase inhibitor is an acetylcholinesterase inhibitor.

14. The method according to claim 13, wherein the acetylcholinesterase inhibitor is selected from the group consisting of galanthamine, physostigmine, tetrahydroamino-acridine (tacrine), citicoline, velnacrine maleate, metrifonate, and heptastigmine.

15. The method according to claim 8, wherein the cholinesterase inhibitor is a butyrylcholinesterase inhibitor.

16. The method according to claim 8, wherein the at least one cholinesterase inhibitor is administered in an amount of from about 20 mg to about 200 mg per day.

* * * * *

(12) EX PARTE REEXAMINATION CERTIFICATE (7956th)
United States Patent
Hutchinson

(10) Number: US 5,965,571 C1
(45) Certificate Issued: Jan. 4, 2011

(54) CHOLINESTERASE INHIBITORS FOR TREATMENT OF PARKINSON'S DISEASE

(75) Inventor: Michael Hutchinson, New York, NY (US)

(73) Assignee: New York University, New York, NY (US)

Reexamination Request:
No. 90/009,489, Jul. 15, 2009

Reexamination Certificate for:
Patent No.: 5,965,571
Issued: Oct. 12, 1999
Appl. No.: 08/915,736
Filed: Aug. 21, 1997

Related U.S. Application Data
(60) Provisional application No. 60/022,746, filed on Aug. 22, 1996.

(51) Int. Cl.
*A61K 45/00* (2006.01)
*A61K 31/55* (2006.01)
*A61K 31/00* (2006.01)
*A61K 45/06* (2006.01)
*A61K 31/407* (2006.01)

(52) U.S. Cl. .................. 514/297; 514/278; 514/32; 514/411; 424/297; 424/489

(58) Field of Classification Search .................. 514/297
See application file for complete search history.

(56) References Cited

PUBLICATIONS

Agnoli et al, "New Strategies in the Management of Parkinson's Disease: A Biological Approach Using a Phospholidid Precursor (CDP–Choline)", *Neuropsychobiology* (1982) vol. 8: 289–296.
Eberhardt et al., "Citicoline in the Treatment of Parkinson's Disease", *Clinical Therapeutics* (1990) vol. 12: 489–495.
Ott et al., "Exacerbation of Parkinsonism by Tacrine", *Clinical Neuropharmacology* (1992) vol. 15: 322–325.
Clough et al., "Cholinergic and Dopaminergic Mechanisms in Parkinson's Disease after Long–Term L–DOPA Administration", *Advances in Neurology* (1984) vol. 40: 131–140.
Tarsy et al., "Physostigmine in Choreiform Movement Disorders", *Neurology* (1974) vol. 24: 28–33.

*Primary Examiner*—Padmashri Ponnaluri

(57) ABSTRACT

Parkinson's disease can be treated with an at least one cholinesterase inhibitor. The cholinesterase inhibitor has been found to alleviate both any symptoms of dementia as well as to reduce rigidity and improve motor function.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 1, lines 36-51:

Several common types of central nervous system dysfunction and peripheral side effects are associated with administration of levodopa. Toxic side effects to the central nervous system include mental changes, such as confusion, agitation, hallucinosis, hallucinations, delusions, depression, mania and excessive sleeping. The symptoms may be related to activation of dopamine receptors in non-striatal regions, particularly the cortical and limbic structures. Elderly patients and patients with cortical Lewy body disease or concomitant Alzheimer's disease are extremely sensitive to small doses of levodopa. However, all patients with Parkinson's disease, regardless of age, can develop psychosis if they take excess amounts of levodopa as a means to overcome "off" periods. This is difficult to remedy, [as reducing the dosage of levodopa may lessen its beneficial influence on motor function] *other than by reducing the dosage of levodopa, thereby possibly lessening the beneficial response of motor function to levodopa as well*.

Column 5, lines 56-61:

Acetycholinesterase inhibitors enhance the effect of acetycholine by either inhibiting its hydrolyzation or by prolonging the actual time that each acetylcholine molecule is present in the synapse. Cholinesterase inhibitors, considered equivalent to anticholinesterase, may also be known as a cholinesterase [agonist] *antagonist*.

Column 6, lines 4-10:

Currently, the known acetylcholinesterase inhibitors available include galanthamine, physostigmine, tetrahydroaminoacridine (tacrine), [citicoline,] velnacrine maleate, metrifonate, and heptastigmine. For purposes of the present invention, "cholinesterase inhibitors" includes acyl cholinesterase inhibitors, including acetylcholinesterase inhibitors and butyryl cholinesterase inhibitors.

Column 6, lines 11-19:

Tacrine, a reversible cholinesterase inhibitor, is known chemically as 1,2,3,4-tetrahydro-9-acridinamine (commonly referred to in clinical and pharmacological literature as THA). Tacrine is an orally bioavailable, centrally active, reversible cholinesterase inhibitor. Presumably, its efficacy lies in its ability to elevate acetylcholine concentrations in the cerebral cortex by [allowing] *inhibiting* the degradation of acetylcholine released by those cholinergic neurons that remain intact.

AS A RESULT OF REEXAMINATION, IT HAS BEEN DETERMINED THAT:

Claims 1, 3-5 and 7 are cancelled.

Claims 6, 8 and 14 are determined to be patentable as amended.

Claims 9, 11-13 and 16, dependent on an amended claim, are determined to be patentable.

New claims 17-19 are added and determined to be patentable.

Claims 2, 10 and 15 were not reexamined.

6. The method according to claim [4] *1*, wherein the cholinesterase inhibitor is a butyrylcholinesterase inhibitor.

8. A method for treating [a patient suffering from] Parkinson's Disease *in a patient in need thereof* consisting of administering to said patient an effective amount of at least one cholinesterase inhibitor [in combination] *wherein said patient is receiving treatment* with at least one medication conventionally administered to treat Parkinson's Disease, *and wherein the dose of said conventional medication is maintained following administration of said at least one cholinesterase inhibitor*.

14. The method according to claim 13, wherein the acetylcholinesterase inhibitor is selected from the group consisting of galanthamine, physostigmine, tetrahydroaminoacridine (tacrine), [citicoline,] velnacrine maleate, metrifonate, and heptastigmine.

*17. A method for treating dementia associated with Parkinson's Disease in a patient in need thereof consisting of administering to said patient an effective amount of at least one cholinesterase inhibitor wherein said patient is receiving treatment with a dopaminergic drug, wherein the dose of said dopaminergic drug is maintained following administration of said at least one cholinesterase inhibitor, and wherein said dementia is not multi-infarct dementia or senile dementia of the Alzheimer's type.*

*18. The method of claim 17, wherein said cholinesterase inhibitor is an acetylcholinesterase inhibitor.*

*19. The method of claim 17, wherein said dopaminergic drug is levodopa.*

\* \* \* \* \*